United States Patent
Hulliger

(10) Patent No.: US 9,938,631 B2
(45) Date of Patent: Apr. 10, 2018

(54) ANODIZING CONTAINER

(71) Applicant: DePuy Synthes Products, Inc., Raynham, MA (US)

(72) Inventor: Urs Hulliger, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 112 days.

(21) Appl. No.: 14/946,392

(22) Filed: Nov. 19, 2015

(65) Prior Publication Data

US 2016/0076163 A1 Mar. 17, 2016

Related U.S. Application Data

(62) Division of application No. 13/466,242, filed on May 8, 2012, now Pat. No. 9,221,563.

(60) Provisional application No. 61/495,124, filed on Jun. 9, 2011.

(51) Int. Cl.

| | | |
|---|---|---|
| C25D 17/06 | (2006.01) | |
| C25D 11/34 | (2006.01) | |
| B65B 5/00 | (2006.01) | |
| C25D 17/08 | (2006.01) | |
| C25D 11/00 | (2006.01) | |
| A61F 2/00 | (2006.01) | |
| A61L 2/07 | (2006.01) | |
| A61B 17/00 | (2006.01) | |
| A61B 50/20 | (2016.01) | |
| A61B 50/30 | (2016.01) | |

(52) U.S. Cl.
CPC ............ *C25D 11/34* (2013.01); *A61F 2/0095* (2013.01); *A61L 2/07* (2013.01); *B65B 5/00* (2013.01); *C25D 11/005* (2013.01); *C25D 17/06* (2013.01); *C25D 17/08* (2013.01); *A61B 50/20* (2016.02); *A61B 50/30* (2016.02); *A61B 2017/00526* (2013.01)

(58) Field of Classification Search
CPC ........................................................ C25D 17/08
See application file for complete search history.

(56) References Cited

U.S. PATENT DOCUMENTS

| | | | | |
|---|---|---|---|---|
| 889,103 | A * | 5/1908 | Buck | C25D 17/08 |
| | | | | 204/297.06 |
| 5,088,609 | A * | 2/1992 | Frye | A47F 5/08 |
| | | | | 118/503 |
| 6,183,513 | B1 | 2/2001 | Guenthner et al. | |
| 6,884,393 | B2 | 4/2005 | Hui et al. | |
| 7,323,096 | B2 * | 1/2008 | Yoshida | B08B 3/14 |
| | | | | 205/101 |

(Continued)

FOREIGN PATENT DOCUMENTS

| | | |
|---|---|---|
| EP | 1 990 447 | 12/2008 |
| GB | 758430 | 3/1956 |

(Continued)

*Primary Examiner* — Bryan D. Ripa
(74) *Attorney, Agent, or Firm* — FAY KAPLUN & MARCIN, LLP

(57) ABSTRACT

A device is for treating and packaging implants. The device includes a container including a chamber therein. The chamber is closed by a removable seal. The device also includes a carrier sized and shaped to be inserted into the chamber. The carrier includes a carrying structure configured to connect an implant thereto. A portion of the carrier may be formed of an electrically conductive material.

14 Claims, 11 Drawing Sheets

(56) References Cited

U.S. PATENT DOCUMENTS

| 7,396,439 | B2 | 7/2008 | Sasaki et al. |
| 2005/0217989 | A1* | 10/2005 | Hradil .................... C25D 17/22 204/201 |
| 2006/0113207 | A1 | 6/2006 | Ryan et al. |
| 2008/0277286 | A1 | 11/2008 | Richardson et al. |

FOREIGN PATENT DOCUMENTS

| JP | 6055940 | 4/1985 |
| JP | 2003/500159 | 1/2003 |
| JP | 50-131820 | 10/2016 |
| WO | 00/72777 | 7/2000 |
| WO | 00/72776 | 12/2000 |
| WO | 03/039609 | 5/2003 |

* cited by examiner

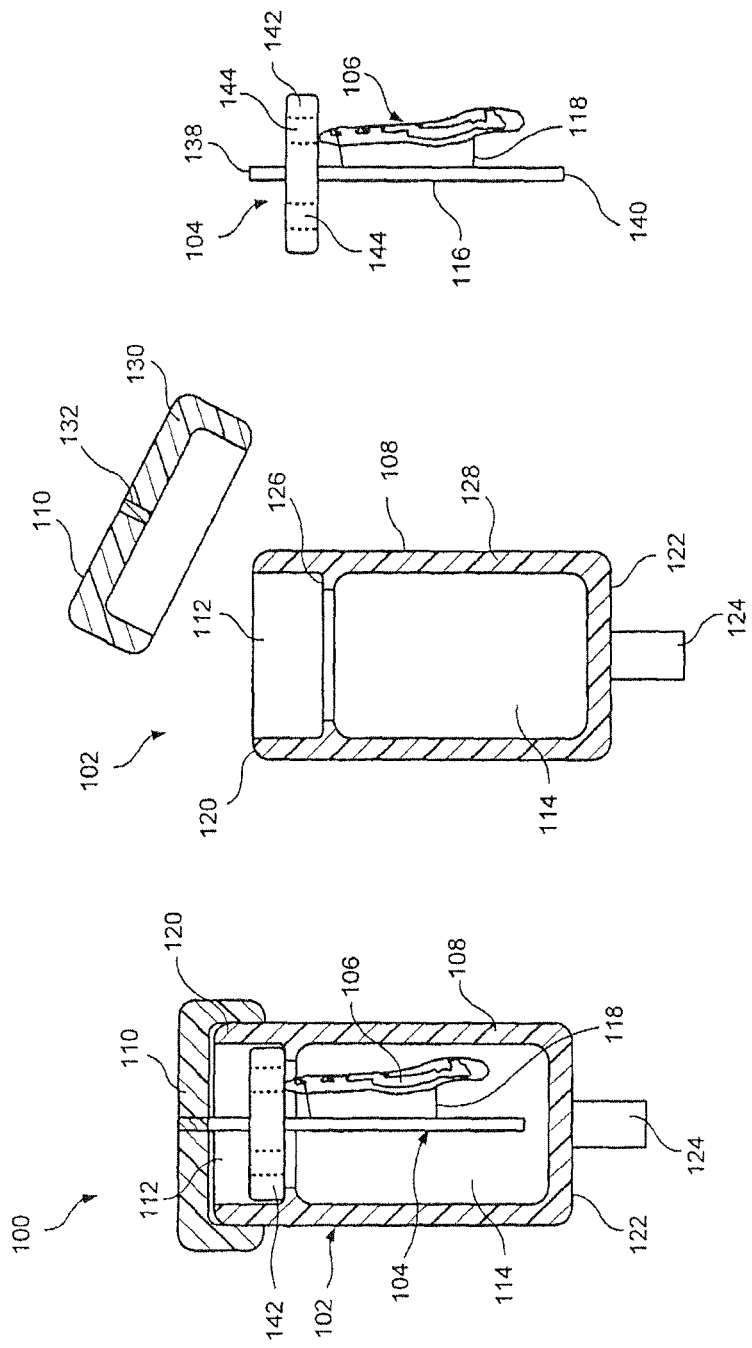

US 9,938,631 B2

ANODIZING CONTAINER

PRIORITY CLAIM

The present application is a Divisional Application of pending U.S. patent application Ser. No. 13/466,242, filed on May 8, 2012, now U.S. Pat. No. 9,221,563; which claims priority to U.S. Provisional Patent Application Ser. No. 61/495,124 filed on Jun. 9, 2011. The disclosures of the above patents/applications are incorporated herein by reference.

BACKGROUND

Implants, such as bone plates, must be sterile prior to use and must remain sterile until implanted in patients. Currently, sterilization and packaging may require different devices and processes, which may be both time consuming and costly.

SUMMARY OF THE INVENTION

The present invention relates to a device for treating and packaging implants, includes a container extending from a first end to a second end and including a chamber therein, the first end including a first opening in fluid communication with the chamber and a removable seal coupled to the first end of the container to close the first opening and a carrier sized and shaped to be inserted into the chamber and including a carrying structure configured to connect the implant thereto, a portion of the carrier being formed of an electrically conductive material.

BRIEF DESCRIPTION OF THE DRAWINGS

FIG. 1 shows a cross-sectional side view of a device according to an exemplary embodiment of the present invention;

FIG. 2 shows a cross-sectional side view of a bottle according to the device of FIG. 1;

FIG. 3 shows a side view of a carrier according to the device of FIG. 1;

DETAILED DESCRIPTION

Figure 4:
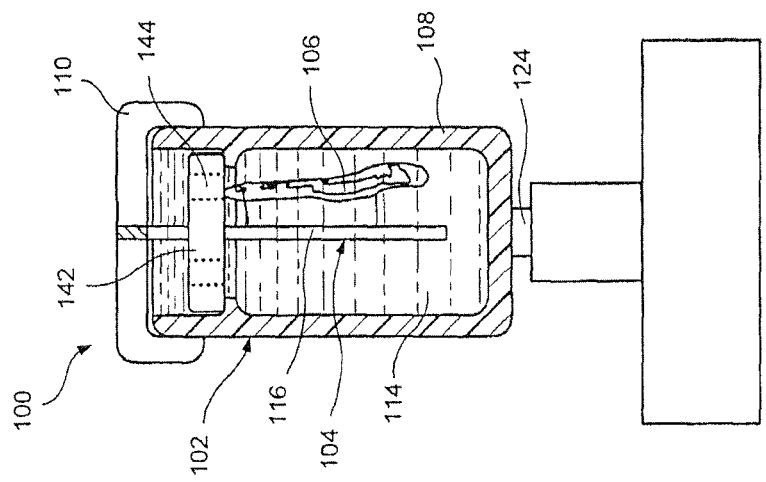
FIG. 4 shows another cross-sectional side view of the device of FIG. 1 connected to positive and negative electrodes.

The present invention may be further understood with reference to the following description and the appended drawings, wherein like elements are referred to with the same reference numerals. The present invention relates to devices for the treatment of bone implants and, in particular, relates to devices for treating bone implants by, for example, electropolishing, anodizing, sterilizing and other suitable treatments for preparing a bone implant for implantation. The present invention relates also to devices for packaging and transporting bone implants. Exemplary embodiments of the present invention describe a device including a container receiving a carrier on which a bone implant is carried during electropolishing, anodization, sterilization, cleaning, drying and transportation. Although the exemplary embodiments and the figures specifically show and describe a bone plate, it will be understood by those of skill in the art that the device of the present invention may be used to sterilize and package any of a variety of medical devices.

As shown in FIGS. 1-7, a device 100 according to an exemplary embodiment of the present invention comprises a container in the from of a bottle 102 configured to receive a carrier 104 which holds an implant 106 thereon so that the implant 106 may be treated and transported within the bottle 102. As shown in FIG. 2, the bottle 102 includes a body 108 having a chamber 114 sized and shaped to receive the carrier 104 and the implant 106 along with a lid 110 for sealing a first opening 112 of the body 108 through which the carrier 104 and the implant 106 are inserted. The carrier 104 may include, for example, an elongate member 116 and a carrying structure 118 such as, for example, a wire extending laterally therefrom to hold the implant 106 during the treatment and transportation process.

The body 108 of the bottle 102 extends longitudinally from a first end 120 to a second end 122 and includes the chamber 114 therein. The first end 120 includes the first opening 112 extending therethrough in fluid communication with the chamber 114. The second end 122 includes a second opening 124 extending therethrough in fluid communication with the chamber 114. As would be understood by those skilled in the art, the chamber 114 may be filled with an electrolytic solution for anodizing the implant 106 and a solution for rinsing the implant 106. The chamber 114 is defined by a wall 128 formed of a material that does not react with or is inert to solutions used for anodizing and rinsing such as, for example, plastic or glass. The material of the wall 128 may be transparent so that the implant 106 is visible therethrough. In one exemplary embodiment, the body 108 and the chamber 114 are substantially cylindrical. It will be understood by those of skill in the art, however, that the body 108 and the chamber 114 may be any of a variety of shapes and sized so long as the chamber 114 is sized and shaped to accommodate the carrier 104 and the implant 106 therein.

The first opening 112 is sized and shaped to permit the carrier 104 and the implant 106 to be passed therethrough into the chamber 114. The chamber 114 may include a shoulder 126 extending radially inward to hold and support a portion of the carrier 104 inserted therein. The second opening 124 is configured to connect the device 100 to a negative electrode 136 (e.g., a cathode). After the implant has been treated, the second opening 124 may be closed and/or sealed for transportation by, for example, melting and/or crimping the opening 124, by closing a valve, inserting a plug, screwing a cap thereover, or by any other known closure method as would be understood by those of skill in the art.

The lid 110 is releasably couplable to the first opening 112 to seal the bottle 102. The lid is releasably coupled using, for example, a bayonet fitting, corresponding threading, press fitting or by any other suitable mechanical coupling. In another embodiment, the lid 110 includes mating male and female parts which engage one another until released via, for example, a pull tab or other breakable mechanism. In yet another embodiment, the lid 110 includes a plurality of apertures while the first end 120 of the body 108 includes a plurality of corresponding recess through which cable ties, or other similar coupling mechanisms, may be used to fix the lid 110 to the body 108. It will be understood by those of skill in the art that a similar lid may also be used to close and/or seal the second opening 124.

The lid 110 according to this embodiment includes an electrically non-conductive portion 130, such as plastic or glass, which does not react with the anodizing and/or rinsing solution filling the chamber 114 and an electrically conductive portion 132 connectable to a positive electrode 134 (e.g., anode) through which electric current may flow into the device 100. The conductive portion 132 may, for example, be centrally located on the lid 110 to align with the elongated member 116 of the carrier 104 when the carrier 104 is placed within the chamber 114 of the body 108 and the lid 110 is closed over the first opening 112.

As shown in FIG. 3, the carrier 104 includes the elongate member 116 which extends longitudinally from a first end 138 to a second end 140 and a supporting structure 142 attached to the elongate member proximate the first end 138. The supporting structure 142 is preferably sized and shaped to engage and/or be seated on the shoulder 126 within the chamber 114. For example, where the chamber 114 is substantially cylindrical, the supporting structure 142 may be disc-shaped and the elongate member 116 may extend through a center thereof. The supporting structure includes a plurality of apertures 144 extending therethrough to permit the anodizing and/or rinsing solutions to flow therethrough. When the supporting structure 142 is seated on the shoulder 126, the first end 138 of the elongate member 116 is substantially aligned with the first end 120 of the body 108 such that when the lid 110 is closed over the first opening 112, the first end 138 of the elongate member 116 contacts the conductive portion 132 of the lid 110. Thus, the lid 110 serves the dual purpose of passing electric current through the conductive portion 132 and into the carrier 104 while also preventing the carrier 104 from moving when the bottle 102 once the lid 110 has been closed.

The carrying structure 118 extends from the elongate member 116 to connect the implant 106 to the carrier 104. As would be understood by those skilled in the art, the carrying structure 118 may be formed of or include an electrically conductive material such as, for example, a wire or a spring, to electrically connect the implant 116 to the carrier 104. The carrier 104 may be entirely formed of an electrically conductive material. Alternatively, the carrier 104 may include an electrically conductive structure such as a channel extending therethrough for electrical connection to the implant 106. In a preferred embodiment, the implant 106 and the carrier 104 are formed of the same material such as, for example, titanium.

According to an exemplary method using the device 100, the implant 106 is attached to the carrier 104 via one or more carrying structures 118, as shown in FIG. 3. The carrier 104 may then be placed within the chamber 114 of the body 108 with the supporting structure 142 seated on the shoulder 126 therewithin. The lid 110 is then closed over the first opening 112 so that the conductive portion 132 contacts the first end 138 of the elongate member 116 of the carrier 104. As shown in FIG. 4, the chamber 114 is filled with an electrolytic solution and the device 100 is connected to positive and negative electrodes 134, 136, respectively. Specifically, the positive electrode 134 is connected to the conductive portion 132 of the lid 110 while the negative electrode 136 is connected to the second opening 124. Upon activation of the electrodes 134, 136 current flows from the positive electrode 134 through the conductive portion 132 of the lid 110, the carrier 104 and the implant 106 to the negative electrode 136 via the electrolytic solution. The solution is permitted to flow through the apertures 144 of the supporting structure 142 of the carrier 104 to anodize the implant 106. Upon completion of the anodizing process, the electrolytic solution may be released via the second opening 124.

Figure 5:
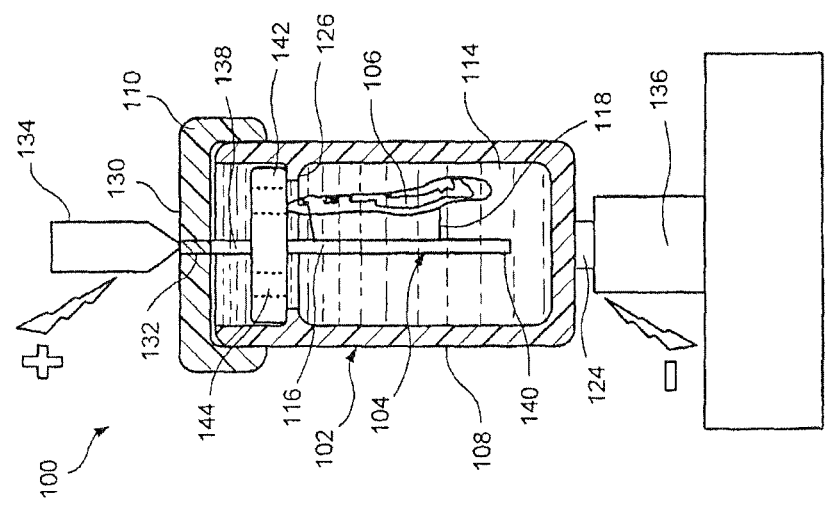
FIG. 5 shows a cross-sectional side view of the device of FIG. 1 filled with a rinsing solution.
Figure 6:
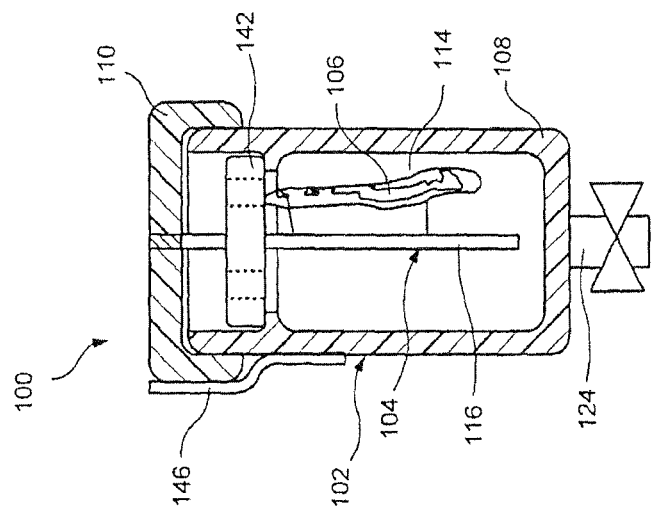
FIG. 6 shows a cross-sectional side view of the device of FIG. 1 in which all openings of the bottle are closed.
Figure 7:
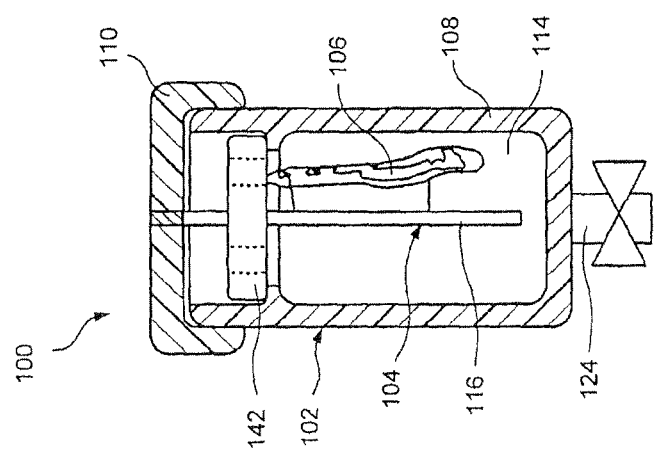
FIG. 7 shows a cross-sectional side view of the device of FIG. 1 sealed and ready for transport.

Once the anodizing process has been completed, the chamber 114 is filled with a rinsing solution via the second opening 124 so that the implant 106 may be rinsed and subsequently dried within the bottle 102, as shown in FIG. 5. As would be understood by those skilled in the art, suitable rinsing solutions include demineralized water or hot water, with or without a detergent. The second opening 124 may then be sealed, as shown in FIG. 6, using any desired closing and/or sealing mechanism as described above. The implant 106 may then be sterilized via standard methods such as, for example, steam sterilization. A label 146 identifying the implant 106 may then be placed on the bottle 102, over the lid 110 and the body 108, as shown in FIG. 7, so that the device 100 may be packaged and prepared for transportation. A user of the implant 106 (e.g., surgeon) will be required to be tear the label 146 to open the bottle 102 by removing the lid 110 such that the carrier 104 may be removed from the chamber 114. Thus, a torn label 146 indicates to a user (e.g., surgeon) that the device 100 may have been opened or tampered with and that the implant 106 may no longer be sterile.

Figure 8:
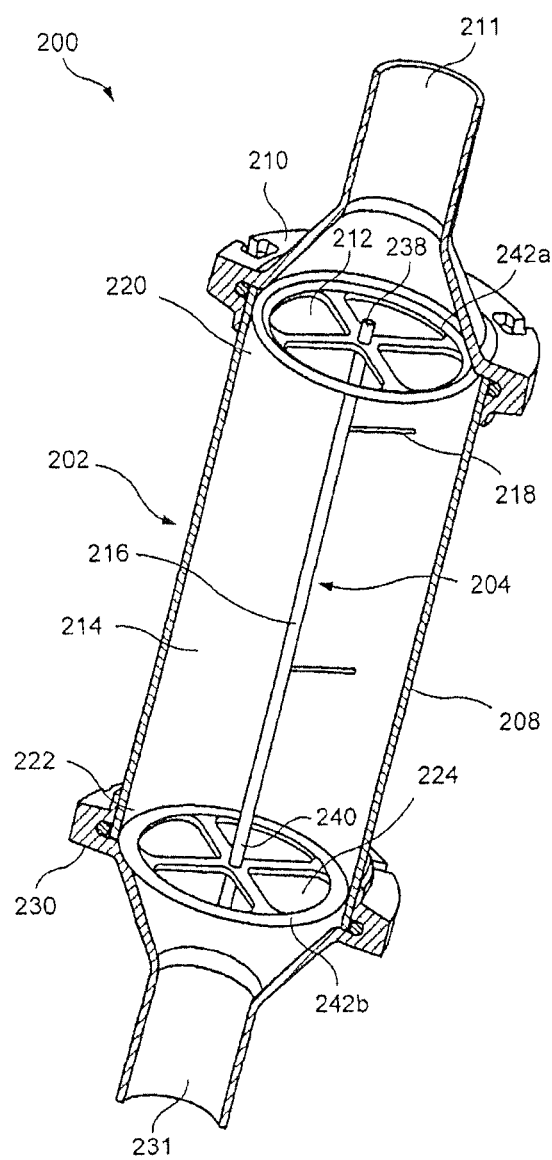
FIG. 8 show a partially cross-sectional perspective view of a device according to another exemplary embodiment of the present invention.

As shown in FIG. 8, a device 200 according to another exemplary embodiment of the present invention is substantially similar to the device 100 comprising a container 202 and a carrier 204 for carrying an implant. The container 202 similarly includes a body 208 having a chamber 214. However, in this embodiment the chamber 214 is defined by a hollow member formed in the exemplary embodiment as a tube including a first opening 212 at a first end 220 and a second opening 224 at a second end 222, each of which is closed by respective lids 210, 230. The lids 210, 230 each include a passageway 211, 231 through which electrodes are arranged when anodization is to be performed. Upon completion of anodization, rinsing and drying of an implant housed therein, the first and second openings already partially closed by the lids 210, 230, which include passageways 211, 231, may be sealed using any of the closing/sealing mechanisms described above in regard to the device 100.

The chamber 214, however, does not include a shoulder therein. In addition, the carrier 204 differs from the carrier 104 in that an elongate member 216 is attached to two supporting structures 242a, 242b. A first supporting structure 242a is attached to a first end 238 of the elongate member 216 while a second supporting structure 242b is attached to a second end of the elongate member 216. An implant may be carried via carrying structures 218, between the first and second supporting structures 242a, 242b. The first and second supporting structures 242a, 242b are sized and shaped to correspond to the chamber 214 such that upon insertion of the carrier 204 into the bottle 208, the implant and carrier 204 are prevented from moving relative thereto. In addition, in the case that the carrier 204 and implant are dropped upon removal from the bottle 202, the size and shape of the supporting structures 242a, 242b prevent the implant from touching the ground.

The device 200 may be used in a manner substantially similar to that described for the device 100 describe above. In particular, in addition to anodization, an implant carried on the carrier 204 may be electropolished, rinsed, dried, sealed and sterilized via, for example, steam sterilization, within the bottle 202 such that the implant is suitable for implantation and remains sterile until use.

Figure 9:
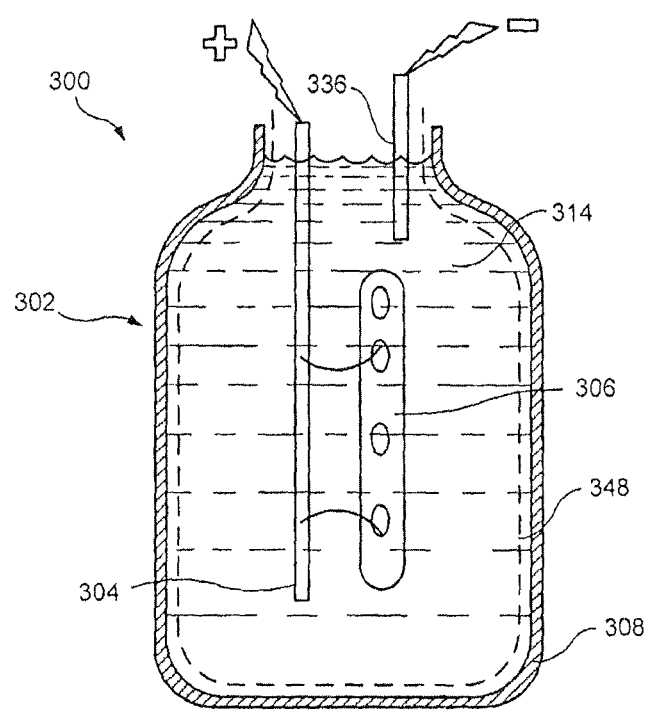
FIG. 9 shows a cross-sectional side view of a device according to yet another exemplary embodiment of the present invention.

As shown in FIG. 9, a device 300 according to yet another exemplary embodiment of the present invention is substantially similar to the device 100 described above, comprising a container in the from of a bottle 302 and a carrier 304 carrying an implant 306. The device 300, however, permits anodization of both the implant 306 and the bottle 302. Similarly to the bottle 102, the bottle 302 includes a body 308 having a chamber 314 sized and shaped to receive the carrier 304 and the implant 306 via a first opening 312. Similarly to the device 100, the carrier 304 and implant 306 are connected to the positive electrode. The body 308 however does not include a second opening. Rather, the chamber 314 includes a sputter coating 348 formed of, for example, titanium, such that the sputter also serves as an anode which reacts under electrical power, protecting the bottle 302 from the anodizing liquids. In addition, a cathode bar 336 is inserted into electrolytic solution filling the chamber 314 and is connected to a negative electrode. In a preferred embodiment, the bottle 302 has a lid through which the cathode bar 336 is inserted. Thus, both the implant 306 and the bottle 302 are anodized and the lid additionally seals the bottle for transportation.

The device 300 may be used in a manner substantially similar to that described above for the device 100. The implant 306 may be electropolished, anodized, rinsed, dried, sealed and sterilized within the bottle 302 such that the implant 306 may be implanted and remains sterile until use.

Figure 10:
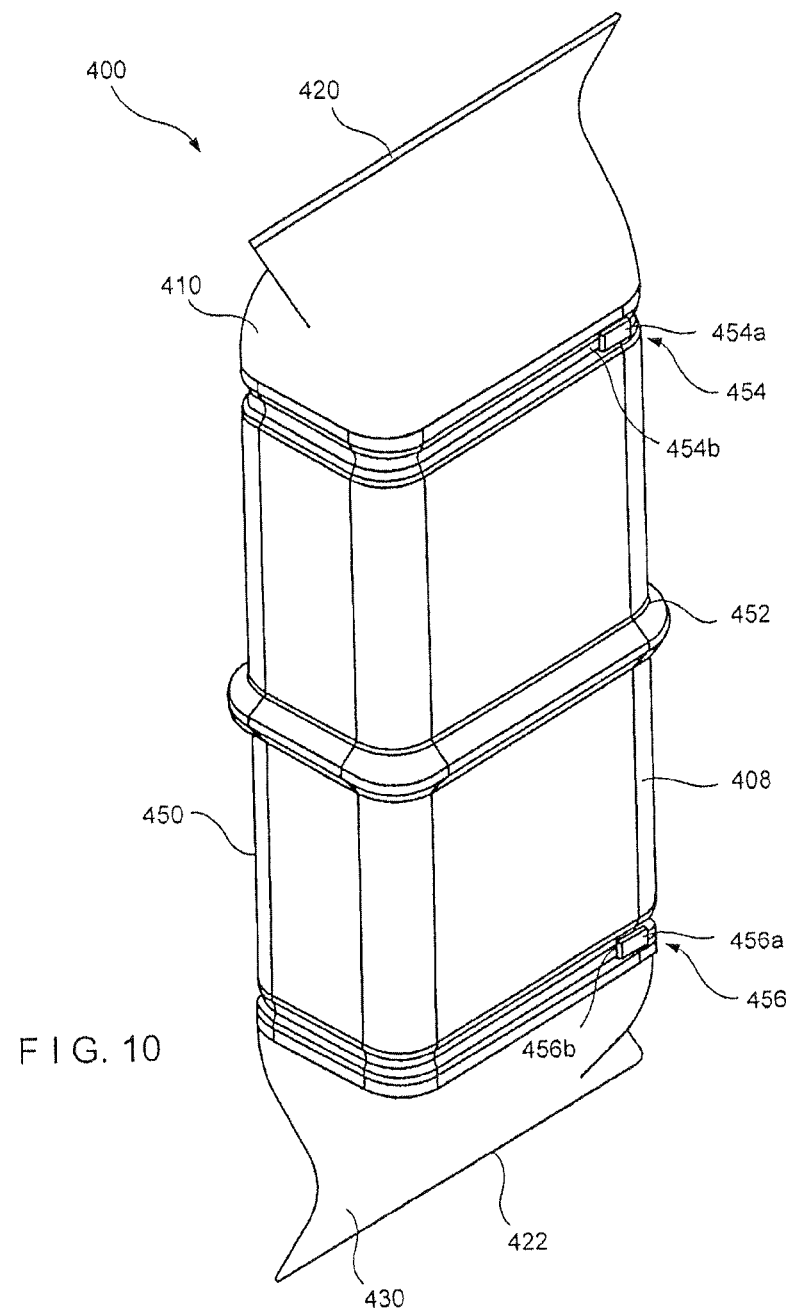
FIG. 10 shows a perspective view of a device according to a still further exemplary embodiment of the present invention in a sealed configuration.
Figure 11:
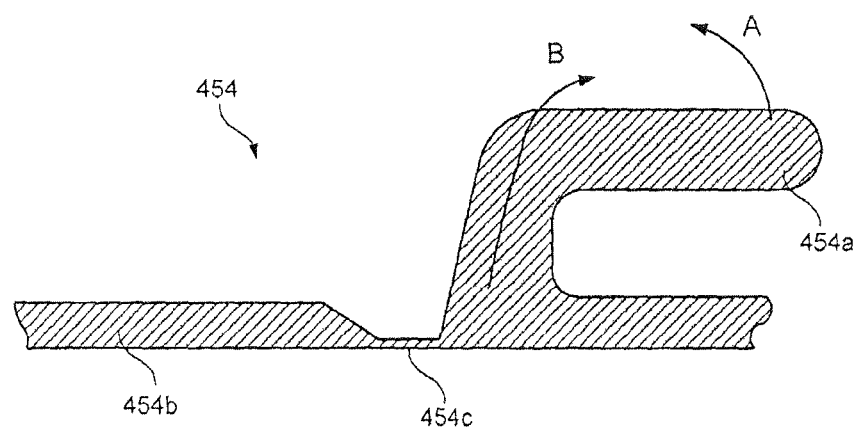
FIG. 11 shows a close-up sectional view of an opening arrangement of the device of FIG. 10.
Figure 12:
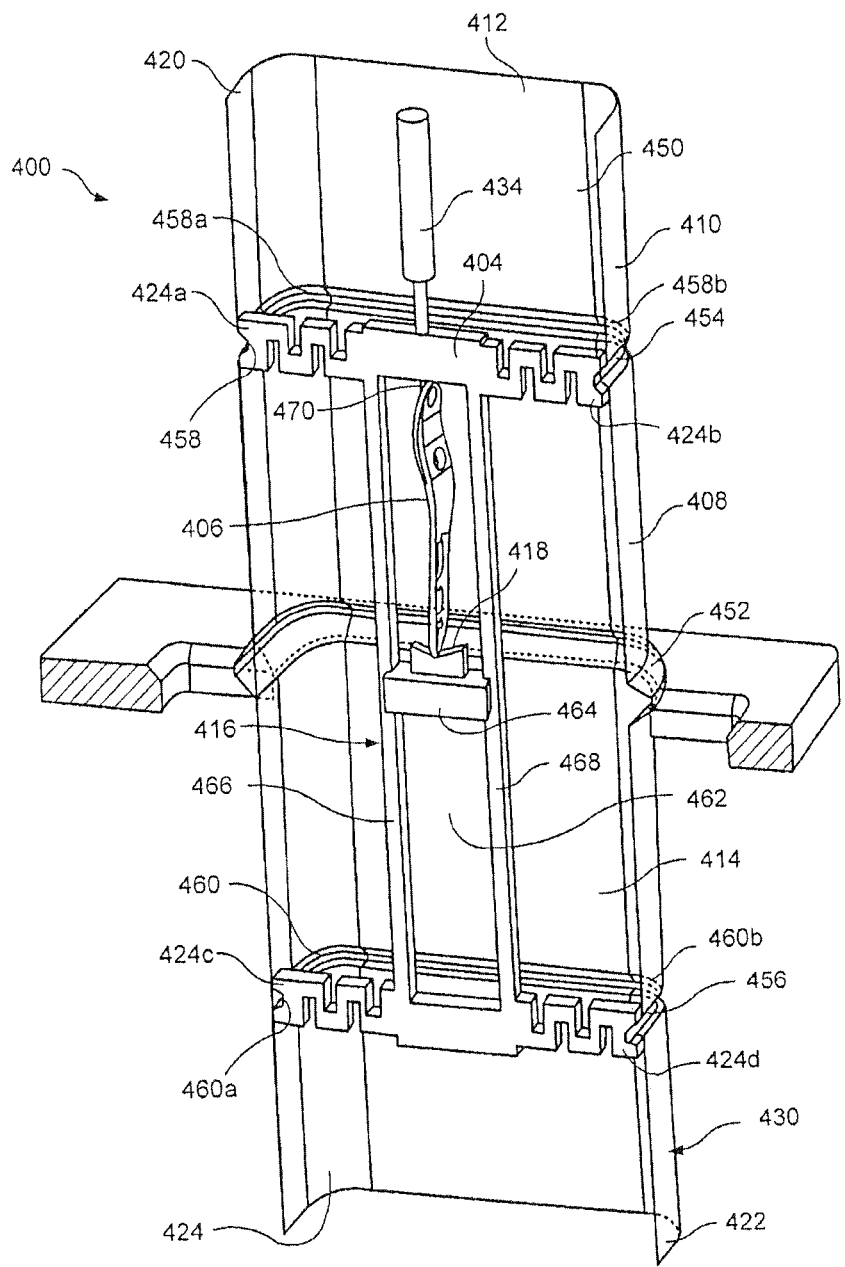
FIG. 12 shows a cross-sectional perspective view of the device of FIG. 10 in an open configuration.

A device 400 according to a still further exemplary embodiment of the present invention is shown in FIGS. 10 to 12. The device 400 is similar to the device 200 described above, comprising a container 402 including a body 408 having a chamber 414 defined by a hollow member 450 and removable end members 410, 430. In contrast to the device 200, the hollow member 450 has a substantially rectangular cross-section comprising, for example, rounded corners. The hollow member 450 further features a lip 452 on its outer surface. The lip 452 is arranged around the outer perimeter of the hollow member 450. The lip 452 is positioned substantially centrally with respect to the first and second ends 420, 422 of the hollow member 450 and, during the electropolishing, rinsing, drying, anodizing, sealing, sterilizing and other suitable processes, rests on a support surface of a processing machine to keep the device 400 in position.

FIG. 10 shows the device 400 in a sealed configuration. The device 400 has removable end members in the form of removable seals 410, 430. The removable seals 410, 430 are formed integrally with the hollow member 450. Each one of the removable seals 410, 430 has an opening arrangement 454, 456. Each opening arrangement 454, 456 has tab 454a, 456a and pull-strip 454b, 456b that may be used to unseal the chamber 414 to allow the carrier 404 to be removed.

FIG. 11 shows a close-up view of the opening arrangement 454. The tab 454a is located at the start of the pull strip 454b. The pull strip 454b extends from the tab around the body 408 and narrows towards a breakpoint 454c that spaces apart the start point and end point of the pull strip 454b. To open the chamber 414, a user pivots the tab 454a about the breakpoint 454c in a direction A. The pivoting action deforms and/or ruptures the breakpoint 454c. The user then pulls the tab 454a in a direction B. The pulling action is then continued to separate the pull strip 454b along a separation pathway that extends around the perimeter of the hollow member 450 from the start point to the end point. FIG. 11 shows a separation pathway arranged for complete removal of a removable seal 410, 430. As those of skill in the art would understand, the device 400 may have any suitable separation pathway provided that the carrier 404 can be removed from the chamber 414.

The opening arrangements 454, 456 are each located in a groove defined in an outer surface of the hollow member 450. As can be seen by FIG. 12 each one of the grooves define a shoulder 458, 460 on an internal surface of the hollow member 450. The shoulders 458, 460 provide a holding arrangement for the carrier 404.

The carrier 404 features a plurality of support structures 424a, 424b, 424c, 424d. The support structures 424a, 424b, 424c, 424d are arms that extend from an elongate member 416 to an end shaped to engage with one of the shoulders 458, 460. For example, when the shoulders 458, 460 are rounded or convex in shape, the ends are complementarily concave in shape. The support structures 424a, 424b, 424c, 424d maintain the position of the carrier 404 in the chamber 414. The support structures 424a, 424b, 424c, 424d are wavy or zigzagged in shape. Due to this shape the arms act like a spring or suspension, which provides some dampening effect during both processing and transportation. Limited relative movement of the carrier 404 along the shoulders 458, 460 is possible during processing and transporting, but the implant 406 is prevented from contacting the inner surface of the chamber 414 due to the rounded corners 458a, 458b, 460a, 460b of the shoulder 458, 460. In an alternative embodiment (not shown) a protrusion or protrusions extends from the elongate member 416 perpendicular to the support structures 424a, 424b, 424c, 424d. The protrusion may extend to the inner surface of the chamber 414 for minimizing or preventing the movement of the carrier 404 relative to the shoulders 458, 460.

The elongate member 416 supports the implant 406 during processing and transporting. The elongate member 416 has an aperture 462 defined therethrough. The aperture 462 is shaped and dimensioned to accommodate the implant 406. The elongate member 416 includes a conductive portion arranged to allow electricity to flow into the implant 406. The carrier 404 has a bridge 464 arranged between elongate bars 466, 468 that define the aperture 462 of the elongate member 416. The carrier 404 has a locating element 470. The bridge 464 and locating element 470 define a carrying structure 418 for carrying the implant 406 therebetween. For this purpose, the bridge 464 and locating element 470 are shaped to abut and hold opposed ends of the implant 406 during processing and transporting.

FIG. 10 shows the device 400 in a closed or sealed configuration in which the device 400 is transported. FIG. 12 shows the device 400 in an open configuration in which the treatment processes are performed. To perform anodization, the electrode 434 is arranged through an opening 412 in an end region of the chamber 414 to contact the conductive portion of the carrier 404 and to connect the carrier 404 to a positive terminal of a power supply. A second opening 424 in the chamber 414 receives a negative electrode therethrough to connect the device 400 to a negative terminal of a power supply. The carrier is then immersed in anodizing fluid and anodizing is performed before rinsing and then drying. The implant may then be treated using other treatment processes as one of skill in the art would understand. To seal the chamber 414 the openings 412, 424 are crimped in an end region and above the opening arrangements 454, 456. In an ideal process the electrode 434 is removed before the sealing process. However, as those of skill in the art would understand, the electrode 434 could remain in the chamber 414 after sealing. If necessary, sterilization can also be performed in the open configuration when the device is in a sterile environment. Alternatively, or in addition, sterilization may be effected, if necessary, through a steam sterilization process.

The carriers 104, 204, 304, 404 have been described for processing and transporting one implant. However, it will be apparent to those skilled in the art that more than one implant can be carried by the carriers 104, 204, 304, 404. For example, the carrier 404 may have two locating elements and the bridge configured to abut and hold two implants. Similarly, the carrier 404 may have another elongate bar for holding three or four implants therebetween. With such a carrier the container may be used to carry more than one implant or an implant and a plurality of screws, for example.

Figures 13, 14:
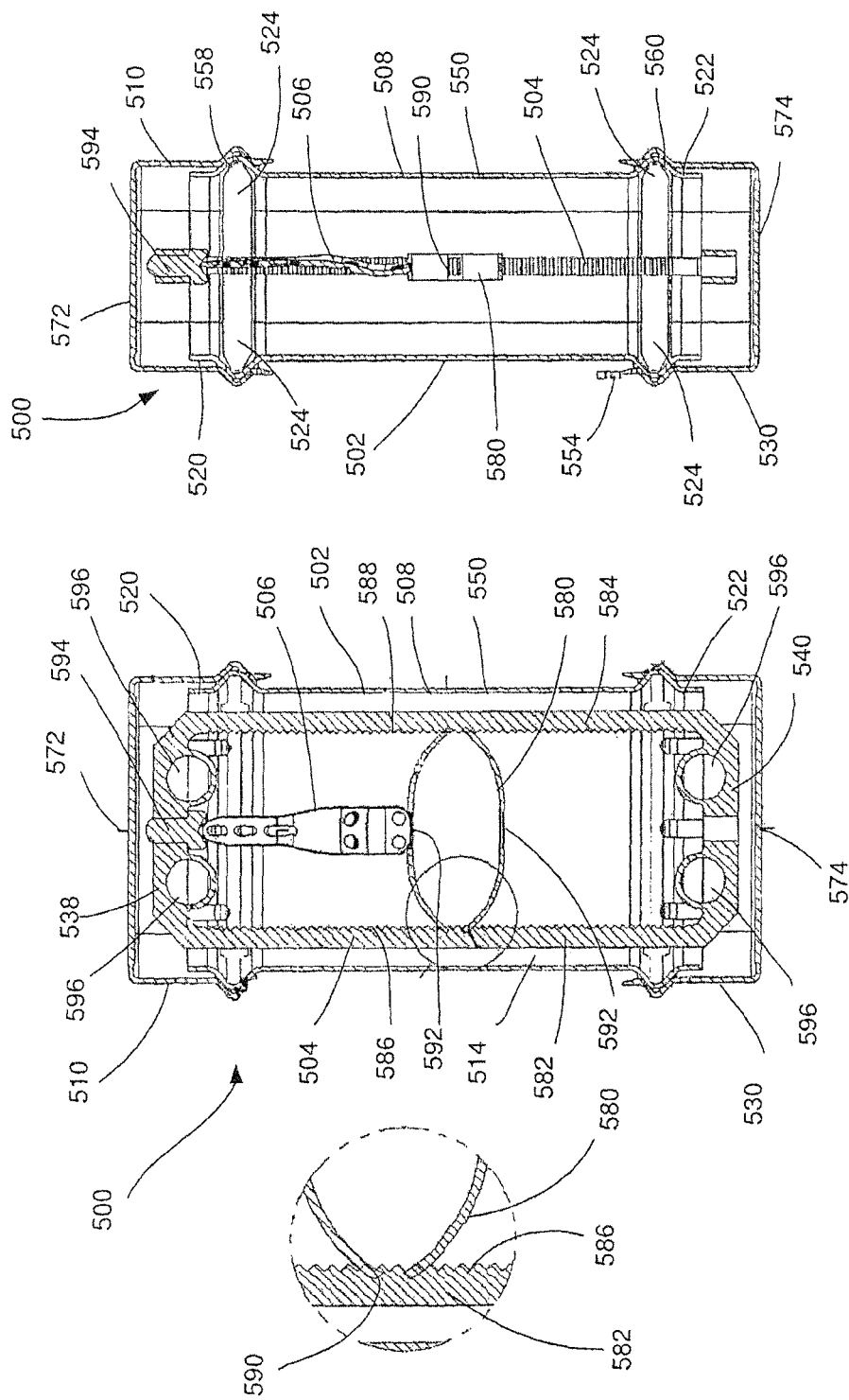
FIG. 13 shows a cross-sectional side view of a device according to another exemplary embodiment of the present invention.
FIG. 14 shows another cross-sectional side view of the device of FIG. 13.
Figure 15:
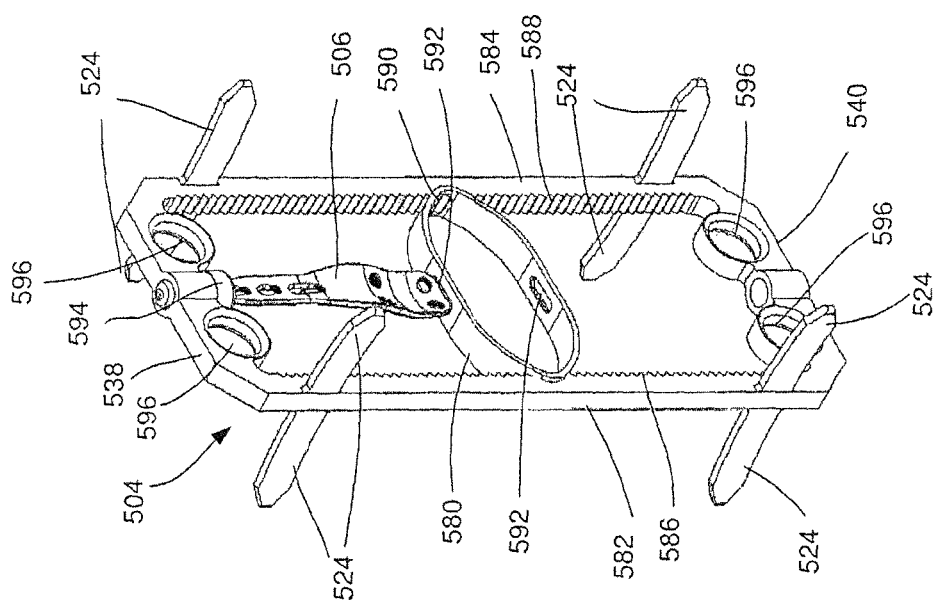
FIG. 15 shows a perspective view of a carrier of the device of FIG. 13.

FIGS. 13-15 show a device 500 according to another exemplary embodiment. Except as specifically pointed out below, the device 500 is substantially similar to the device 400 described above, comprising a container 502 including a body 508 having a chamber 514 sized and shaped to receive a carrier 504 and an implant 506 therein. Similarly to the container 402, the chamber 514 is defined by a hollow member 550 and removable end members 510, 530. The hollow member 550 may have a substantially rectangular cross-section. The end members 510, 530 may be in the form of removable seals, which are formed integrally with the hollow member 550. One of the removable end member 510, 530 may have an opening arrangement such as a tear strip 554 which may be used to unseal the chamber 514 to allow the carrier 504 to be removed. The end members 510, 530 may include a gas and/or steam permeable membrane 572, 574, respectively, such that the implant 506 may be sterilized using steam sterilization.

Rather than including an elongate structure for holding the implant 506, however, the carrier 504, as shown in FIG. 15, is formed of a rigid frame 516 including four sides 538, 540, 582, 584 such that the frame 516 is sized and shaped to be received within the chamber 514. The four sides 538, 540, 582, 584 are attached to one another in a substantially rectangular configuration such that the each of the sides 538, 540, 582, 584 are substantially perpendicular to one another. The frame 516 is received within the body 508 of the container 502 with the first side 538 positioned at a proximal end 520 of the body 508 and the second side 540 positioned at a distal end of the body 508. The frame 516 holds the implant 516 within an interior 578 thereof formed between the sides 538, 540, 582, 584 via a spring holder 580 which engages teeth 586, 588 along an interior of sides 582, 584, respectively, via a ratchet mechanism, as shown in FIG. 13. Thus, the holder 580 may move longitudinally within the frame 516 to accommodate implants of varying lengths and sizes.

The holder 580 may be configured as, for example, a closed loop including openings 590 on opposing sides thereof for engaging the teeth 586, 588. The holder 580 also includes an elongated opening 592 extending therethrough along a portion of the holder 580 between the openings 590. The elongated opening 592 is sized and shaped to seat one end of the implant 506. The holder 580 includes two elongated openings 592 on opposing sides of the holder 580 permitting the implant 506 to be held between the holder 580 and either of the first and second sides 538, 540. At least one of the first and second sides 538, 540 includes a holding structure 594 including a concave surface to seat the other end of the implant 506. Thus, the holder 580 may be moved longitudinally along the frame 516 to hold the implant 506 between the holding structure 594 of one of the first and second sides 538, 540 and the elongate opening 592 of the holder 580. Once the anodizing process is completed, other treatment processes may be performed if necessary. Suitable treatment processes include, but are not limited to, electropolishing, rinsing, drying, sealing and sterilizing. Upon a required use of the implant 506, the implant 506 may be removed therefrom by simply ratcheting the holder 580 away from the implant 506, thereby releasing the implant from between the holder 580 and one of the sides 538, 540. Alternatively, the holder 580 may be spring biased and the user may simply grasp and deform the holder 580 against the bias to release the implant from the holder 580. The removal could be by a user in the operating room after the device 500 has been transported.

The carrier 504 also includes finger holes 596 extending through the first side 538 and/or second side 540 to facilitate removal of the carrier 504 from the proximal end 520 and/or distal end 522 distal of the container 502. The carrier 504 may also include support structures 524 extending laterally therefrom to engage a portion of the body 508 such that the support structures 524 prevent the carrier 504 from moving within the chamber 514. The support structures 524 extend proximate the first and second sides 538, 540 to engage corresponding portions of the container 502 at the proximal and distal ends 520, 522. The corresponding portions of the container 502 may include, for example, a first groove 558 extending about a perimeter of the body 508 proximate the proximal end 520 of the body 508 and a second groove 560 extending about a perimeter of the body 508 proximate the distal end 522 of the body 508. The first and second grooves 558, 560 are sized and shaped to engage the protrusions 524 therein to prevent the carrier 504 from moving within the chamber 514.

Figure 16:
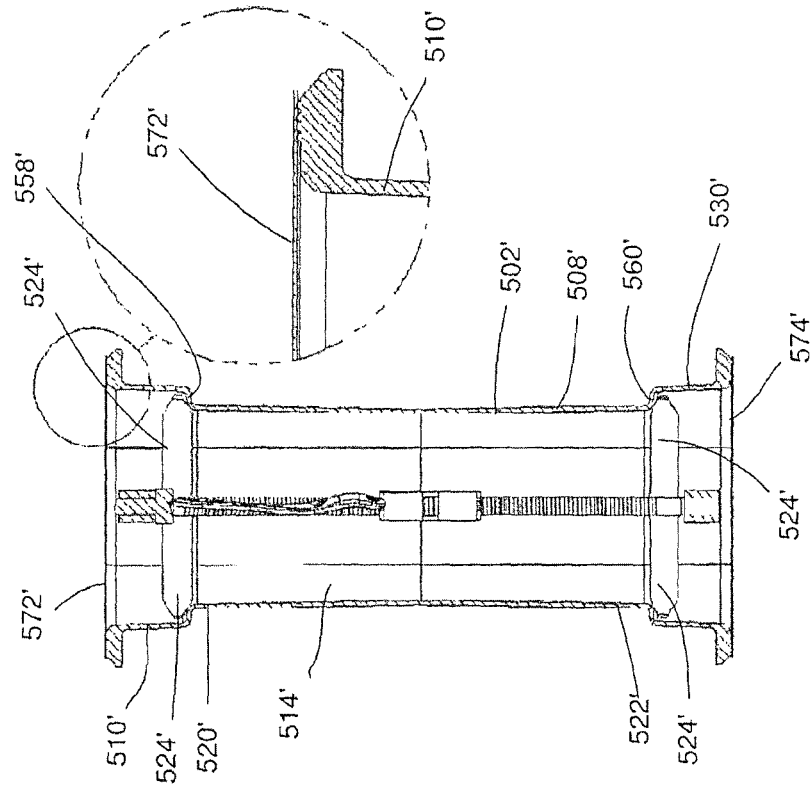
FIG. 16 shows a cross-sectional side view of a device according to an alternate embodiment of the present invention.
Figure 17:
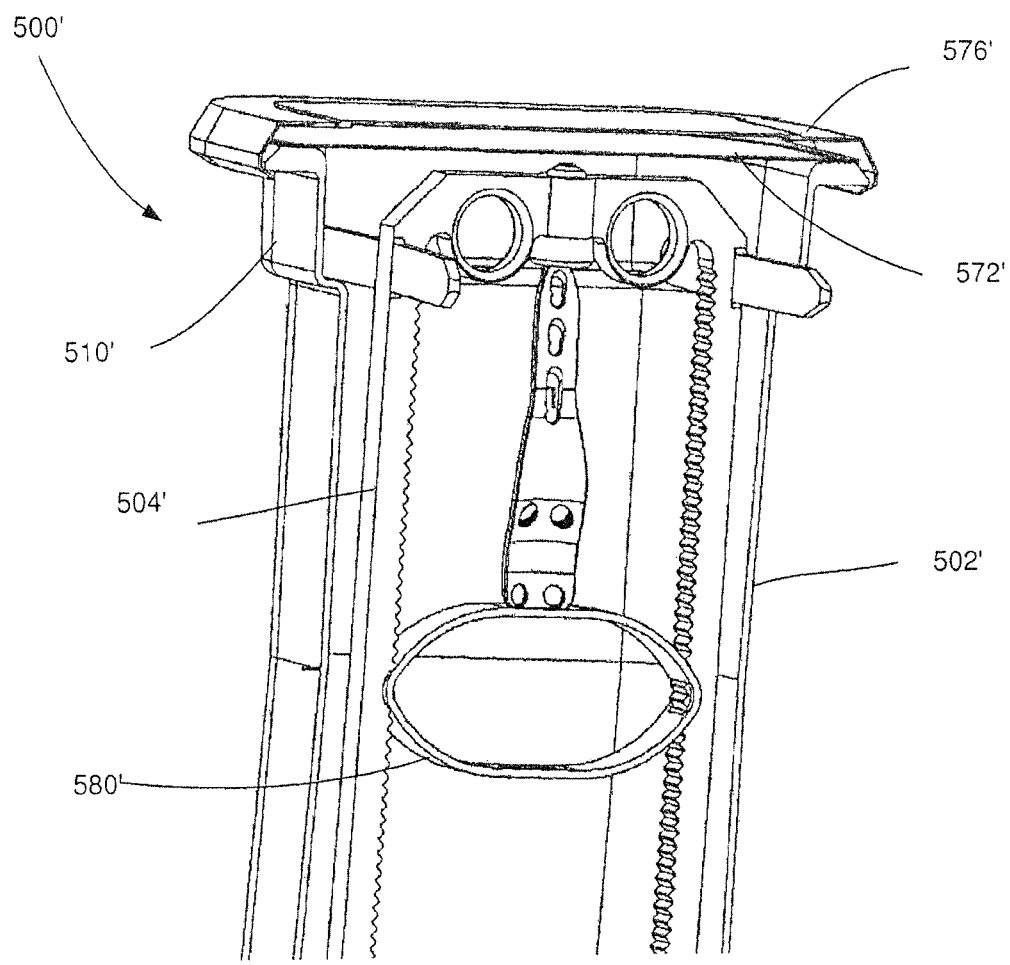
FIG. 17 shows an enlarged cross-sectional perspective view of the device of FIG. 16.

As shown in FIGS. 16-17, a device 500' according to a further embodiment of the invention is substantially similar to the device 500 except as noted below. The device 500' includes a container 502' including a body 508' formed with a chamber 514' sized and shaped to receive a carrier 504' therein. The container 502' may be substantially similar to the container 502 described above except that, rather than first and second grooves, the container 502' includes a first shoulder 558' positioned proximate a proximal end 520' of the body 508' and a second shoulder 560' positioned proximate a distal end 522' of the body 508'. The first and second shoulder 558', 560' are configured such that protrusions 524' extending from the carrier 504' may be seated therein to prevent the carrier 504' from moving relative to the container 502'. Similarly to the container 502, the container 502' also includes end members 510', 530' coupled to the proximal and distal ends 520', 522', respectively, and including steam permeable membranes 572', 574'. The end members 510', 530', however, are configured to be removably coupled to a protective cover 576', as shown in FIG. 17, which extends over the steam permeable membranes 572', 574' of the end members 510', 530' to protect the membranes 572', 574' from being inadvertently ruptured, pierced or penetrated. Although only one cover 576' is shown, it will be understood by those of skill in the art that the device 500' may include two covers 576' to cover each of the permeable membranes 572', 574'. It will also be understood by those of skill in the art that although the cover 576' is only shown with the device 500', the device 500 may also be adapted to include a protective cover couplable to the first and second end members 510, 530 to extend over the steam permeable membranes 572, 574.

The devices 500, 500' may be used in a manner substantially similarly to that described above in regard to the system 100. The device 500, however, permits sterilization of the implant 506 to be achieved via the steam permeable membranes 572, 574. Upon anodization/sterilization, the implant 506 may be sealed within the container 502 until it is ready for use.

It will be apparent to those skilled in the art that modifications and variations can be made in the structure and the methodology of the present invention, without departing from the spirit or the scope of the invention. Thus, it is intended that the present invention cover the modifications and variations of this invention provided that the come within the scope of the appended claims and their equivalents.

What is claimed is:

1. A system for treating a surface of and packaging implants, comprising:
    a container, including:
        a body extending from a first end of the body to a second end of the body and including a chamber therein, the first end of the body including a sealable first opening in fluid communication with the chamber; and
        a carrier sized and shaped to be inserted into the chamber and including a carrying structure configured to connect the implant thereto, a portion of the carrier being formed of an electrically conductive material,
        wherein the carrier includes an elongate member extending from a first end of the elongated member to a second end of the elongated member, the elongate member including the carrying structure,
        wherein the carrier includes a first supporting structure at the first end of the elongate member, and
        wherein the body of the container includes a shoulder extending radially inward from a wall of the chamber such that when the carrier is inserted therein, the first supporting structure engages the shoulder;
    a first electrode configurable in electrical communication with the portion of the carrier formed of an electrically conductive material; and
    a second electrode configurable in electrical communication with a fluid received within the chamber.

2. The system of claim 1, wherein the carrier includes a second supporting structure at the second end of the elongate member.

3. The system of claim 1, wherein the container includes a sealable second opening at the second end of the body, the second opening configured to receive the second electrode.

4. The system of claim 1, wherein the container is substantially hollow.

5. The system of claim 1, wherein the carrying structure is defined by an aperture in the carrier, the aperture having a first and a second end shaped to locate an implant therebetween.

6. The system of claim 1, wherein the body has a substantially rectangular cross-section.

7. The system of claim 1, wherein the body includes a lip extending about an outer perimeter thereof, the lip configured to rest on a support surface of a processing machine.

8. The system of claim 1, wherein the body includes a first removable end member at the first end of the body, the first removable end member configured to be removed from a remaining portion of the body via a first opening arrangement.

9. The system of claim 8, wherein the first opening is configured to be sealed via a crimping of the first removable end member.

10. The system of claim 8, wherein the first opening arrangement includes a pull tab and pull strip.

11. The system of claim 1, wherein the first supporting structure has one of a wavy and zig-zagged shape to provide suspension of the carrier within the chamber.

12. A system for treating a surface of and packaging implants, comprising:
    a container, including:
        a body extending from a first end to a second end and including a chamber therein, the first end including a sealable first opening in fluid communication with the chamber, wherein the body includes a first removable end member at the first end, the first removable end member configured to be removed from a remaining portion of the body via a first opening arrangement, and a second removable end member at the second end, the second removable end member configured be removed from a remaining portion of the body via a second opening arrangement; and
        a carrier sized and shaped to be inserted into the chamber and including a carrying structure configured to connect the implant thereto, a portion of the carrier being formed of an electrically conductive material;
    a first electrode configurable in electrical communication with the portion of the carrier formed of an electrically conductive material; and
    a second electrode configurable in electrical communication with a fluid received within the chamber, wherein the container includes a sealable second opening at the second end thereof, the second opening configured to receive the second electrode.

13. The system of claim 12, wherein the second opening is configured to be sealed via a crimping of the second removable end member.

14. The system of claim 12, wherein the second opening arrangement includes a pull tab and a pull strip.

* * * * *